(12) United States Patent
Ramos-Stanbury

(10) Patent No.: US 7,396,369 B2
(45) Date of Patent: Jul. 8, 2008

(54) 2,3-DISUBSTITUTED PRIMARY PARA-PHENYLENEDIAMINES AND PROCESS FOR OXIDATION DYEING OF KERATIN FIBERS

(75) Inventor: Laure Ramos-Stanbury, Sceaux (FR)

(73) Assignee: L'Oreal S.A., Paris (FR)

( * ) Notice: Subject to any disclaimer, the term of this patent is extended or adjusted under 35 U.S.C. 154(b) by 202 days.

(21) Appl. No.: 11/475,984

(22) Filed: Jun. 28, 2006

(65) Prior Publication Data

US 2007/0011823 A1    Jan. 18, 2007

(30) Foreign Application Priority Data

Jun. 28, 2005    (FR) .................................. 05 06566

(51) Int. Cl.
*A61Q 5/10*    (2006.01)
(52) U.S. Cl. ...................... 8/405; 8/406; 8/408; 8/410; 8/411; 8/412; 8/435
(58) Field of Classification Search .................... 8/405, 8/406, 408, 410, 411, 412, 435
See application file for complete search history.

(56) References Cited

U.S. PATENT DOCUMENTS

| | | | |
|---|---|---|---|
| 4,823,985 A | 4/1989 | Grollier et al. | |
| 4,979,961 A | 12/1990 | Junino et al. | |
| 5,032,137 A | 7/1991 | Junino et al. | |

FOREIGN PATENT DOCUMENTS

| | | | |
|---|---|---|---|
| EP | 1 433 470 A1 | 6/2004 | |
| FR | 2 586 913 A1 | 3/1987 | |
| FR | 2 630 438 A1 | 10/1989 | |
| WO | WO 9012562 A1 * | 11/1990 | |
| WO | WO 2005/051336 A1 | 6/2005 | |
| WO | WO 2006/018089 A1 | 2/2006 | |

OTHER PUBLICATIONS

STIC Search Report dated on Mar. 5, 2008.*
English Abstract of the Patent WO 9012562 A1.*
French Search Report for FR 0506566, dated Apr. 28, 2006.
Database Beilstein, Beilstein Institute for Organic Chemistry, Frankfurt-Main, DE; Morgan: XP002379018, Database accession No. 8265391. (1904).
English language abstract of EP 1 433 470 A1, Jun. 30, 2004.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

Disclosed herein are para-phenylenediamine compounds of formula (I), and their salts and solvates:

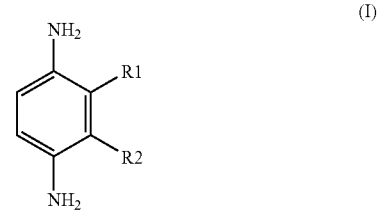

(I)

wherein $R_1$ and $R_2$ form, together with the carbon atoms to which they are attached, a 4-, 5-, 6- or 7-membered ring, wherein the ring comprises carbon atoms and, optionally, one or two atoms chosen from oxygen and nitrogen, the ring being optionally substituted, with the proviso that when the ring comprises two atoms chosen from oxygen and nitrogen, these two atoms are non-adjacent. Compositions comprising these compounds and processes of making them, as well as processes and kits for dyeing keratin fibers are also disclosed.

34 Claims, No Drawings

2,3-DISUBSTITUTED PRIMARY PARA-PHENYLENEDIAMINES AND PROCESS FOR OXIDATION DYEING OF KERATIN FIBERS

CROSS-REFERENCE TO RELATED APPLICATIONS

This application claims benefit of priority under 35 U.S.C. § 119 to French Patent Application No. FR 05 06566, filed Jun. 28, 2005, the contents of which are incorporated herein by reference.

FIELD OF THE INVENTION

Disclosed herein are novel 2,3-disubstituted primary para-phenylenediamines. Also disclosed herein is a composition for the oxidation dyeing of keratin fibers, for example, human keratin fibers such as the hair, comprising, as oxidation base, at least one 2,3-disubstituted primary para-phenylenediamine. Further disclosed herein is a process for oxidation dyeing of keratin materials comprising applying a composition of the present disclosure to the keratin materials.

BACKGROUND OF THE INVENTION

It is known practice to dye keratin fibers, for example, human hair, with dye compositions comprising oxidation dye precursors, for instance, ortho- and para-phenylenediamines, ortho- or para-aminophenols, and heterocyclic compounds such as diaminopyrazole derivatives, generally called oxidation bases. Oxidation dye precursors, or oxidation bases, are colorless or weakly colored compounds which, when combined with oxidizing products, can give rise, by means of an oxidative condensation process, to colored and coloring compounds.

It is also known that the shade obtained with these oxidation bases can be varied by combining them with couplers or coloration modifiers, the latter being chosen, for example, from aromatic meta-diamines, meta-aminophenols, meta-diphenols, and certain heterocyclic compounds.

The variety of molecules available as oxidation bases and couplers makes it possible to obtain a rich palette of colors.

"Permanent" dyeing obtained by virtue of these oxidation dyes ideally satisfies at least one of certain characteristics. For example, the dye ideally has no drawbacks in terms of toxicology, makes it possible to obtain shades with the desired intensity, exhibits good resistance to outside agents (for instance, light, bad weather, washing, permanent-waving, perspiration, and/or rubbing), makes it possible to cover white hairs, is as unselective as possible, i.e., makes it possible to obtain the smallest possible differences in coloration along the same keratin fiber, which may be differently sensitized (i.e., damaged) from its tip to its root, and exhibits good chemical stability in the formulations and a good toxicological profile.

Furthermore, for certain applications, it is desirable to have dyes that give chromatic shades on the hair.

DETAILED DESCRIPTION OF THE INVENTION

The present inventor has discovered, surprisingly, that it is possible to obtain dyes which are capable of producing strong colorations, may be relatively unselective, and may exhibit excellent properties of resistance to the various attacks that the keratin fibers may be subjected to, comprising, as oxidation base, at least one compound chosen from 2,3-disubstituted primary para-phenylenediamines of formula (I) below and the physiologically acceptable salts and solvates thereof.

Disclosed herein are 2,3-disubstituted primary para-phenylenediamines of formula (I):

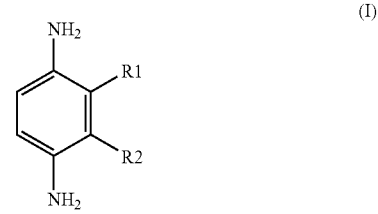

wherein $R_1$ and $R_2$ form, together with the carbon atoms to which they are attached, a 4-, 5-, 6-, or 7-membered ring, wherein the ring comprises carbon atoms and, optionally, one or two atoms chosen from oxygen and nitrogen, and when the ring comprises two atoms chosen from oxygen and nitrogen, then these two atoms are non-adjacent, it being possible for the ring to be substituted, for example, with at least one radical chosen from $C_1$-$C_6$ alkyl, hydroxyl (—OH), $C_1$-$C_6$ alkoxy, amino (—NH$_2$), $C_1$-$C_6$ (mono or dialkyl)amino, and amino($C_1$-$C_6$)alkyl radicals, with the proviso that the compound of formula (I) is not chosen from the following compounds:

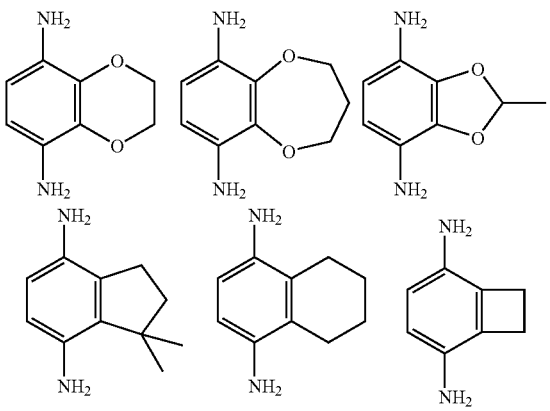

Also disclosed herein are the solvates and salts of physiological acceptable organic or inorganic acids of the compounds of formula (I).

The addition salts may be chosen from acid addition salts, such as hydrochloric acid, hydrobromic acid, sulphuric acid, citric acid, succinic acid, tartaric acid, lactic acid, methanesulphonic acid, para-toluenesulphonic acid, benzenesulphonic acid, phosphoric acid, and acetic acid addition salts.

The compounds of formula (I) may also be in the form of solvates, for example, hydrates or solvates of linear or branched alcohols, such as ethanol and isopropanol.

When the ring formed by $R_1$ and $R_2$ comprises one or two nitrogen atoms, the ring may comprise a nitrogenous divalent radical chosen from —NH— and —N($C_1$-$C_4$ alkyl)- radicals.

According to one embodiment, $R_1$ and $R_2$ may form, together with the carbon atoms to which they are attached, a 5- or 6-membered ring comprising, for example, carbon atoms and, optionally, an entity chosen from oxygen and nitrogenous radicals, for example, (—NH—) or —NMe- radicals.

In another embodiment, $R_1$ and $R_2$ may form, together with the carbon atoms to which they are attached, a 5- or 6-membered ring comprising carbon atoms and, optionally, a nitrogenous radical chosen from (—NH—) and —NMe- radicals.

According to a further embodiment, the ring formed by $R_1$ and $R_2$ may be substituted with 1, 2, or 3 radicals, which may be identical or different, chosen from $C_1$-$C_3$ alkyl, hydroxyl (—OH), amino (—NH$_2$), and amino($C_1$-$C_3$)alkyl radicals. Examples of suitable radicals include, but are not limited to, amino, hydroxyl, methyl, ethyl, isopropyl, n-propyl, and aminomethyl radicals.

In yet another embodiment, the ring is substituted with 1 or 2, for example, 1, radicals chosen from amino, hydroxyl, propyl, aminomethyl, and methyl radicals.

According to a still further embodiment, the ring formed by $R_1$ and $R_2$ may be a carbon-based ring, for example, a carbon-based ring comprising 5 to 6 ring members.

Non-limiting examples of para-phenylenediamines of formula (I), include the following compounds and the addition salts and/or solvates thereof.

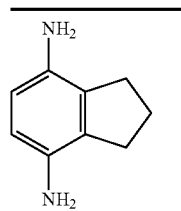 Indan-4,7-diamine

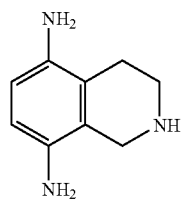 1,2,3,4-Tetrahydroisoquinoline-5,8-diamine

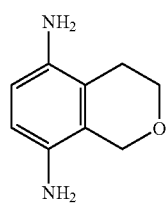 Isochroman-5,8-diamine

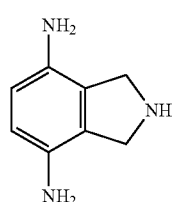 2,3-Dihydro-1H-isoindole-4,7-diamine

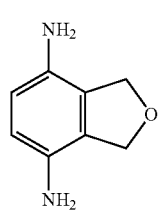 1,3-Dihydroisobenzofuran-4,7-diamine

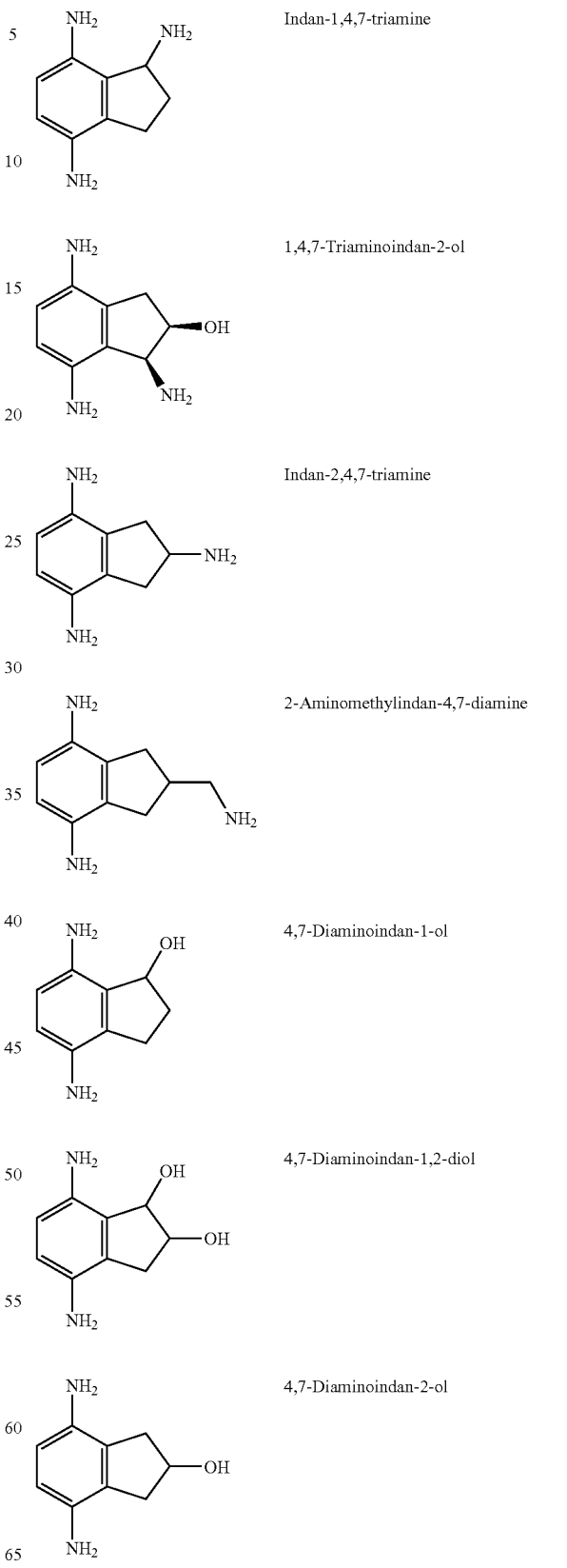

-continued

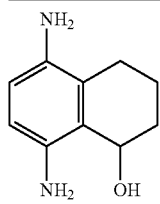 5,8-Diamino-1,2,3,4-tetrahydronaphthalen-1-ol

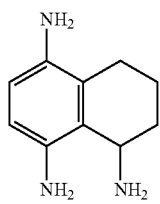 5,6,7,8-Tetrahydronaphthalene-1,4,5-triamine

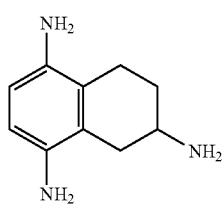 5,6,7,8-Tetrahydronaphthalene-1,4,6-triamine

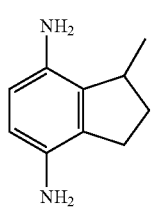 1-Methylindan-4,7-diamine

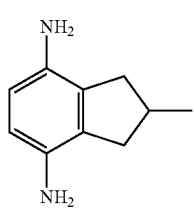 2-Methylindan-4,7-diamine

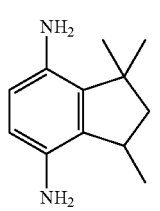 1,1,3-Trimethylindan-4,7-diamine

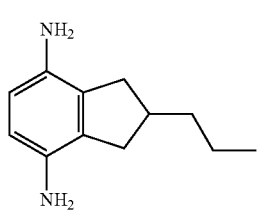 2-Propylindan-4,7-diamine

-continued

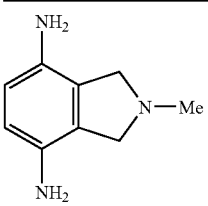 2-Methylisoindoline-4,7-diamine

In one embodiment, the 2,3-disubstituted primary para-phenylenediamines of formula (I) may be chosen from:

indan-4,7-diamine, 1,2,3,4-tetrahydroisoquinoline-5,8-diamine, 2,3-dihydro-1H-isoindole-4,7-diamine, 2-methylisoindoline-4,7-diamine, indan-2,4,7-triamine, 2-aminomethylindan-4,7-diamine, 4,7-diaminoindan-2-ol, 2-methylindan-4,7-diamine and 2-propylindan-4,7-diamine, and the physiologically acceptable salts and solvates thereof.

Also disclosed herein is a process for the synthesis of a para-phenylenediamine compound of formula (I), comprising reducing the corresponding intermediate compound of formula (II):

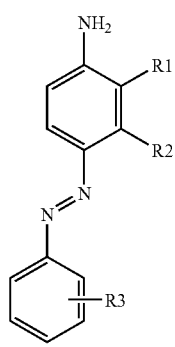

(II)

wherein $R_1$ and $R_2$ form, together with the carbon atoms to which they are attached, a 4-, 5-, 6-, or 7-membered ring, wherein the ring comprises carbon atoms and, optionally, one or two atoms, which may be identical or different, chosen from oxygen and nitrogen, and when the ring comprises two atoms chosen from oxygen and nitrogen, then these two atoms are non-adjacent, it being possible for the ring to be substituted, for example, with at least one radical, which may be identical or different, chosen from $C_1$-$C_6$ linear or branched alkyl, hydroxyl (—OH), $C_1$-$C_6$ alkoxy, amino (—$NH_2$), $C_1$-$C_6$ (mono or dialkyl)amino, and amino($C_1$-$C_6$)alkyl radicals; and $R_3$ is chosen from hydrogen, sulphonic groups, and $C_1$-$C_4$ linear or branched alkyl radicals, with the proviso that the compound of formula (II) is not chosen from:

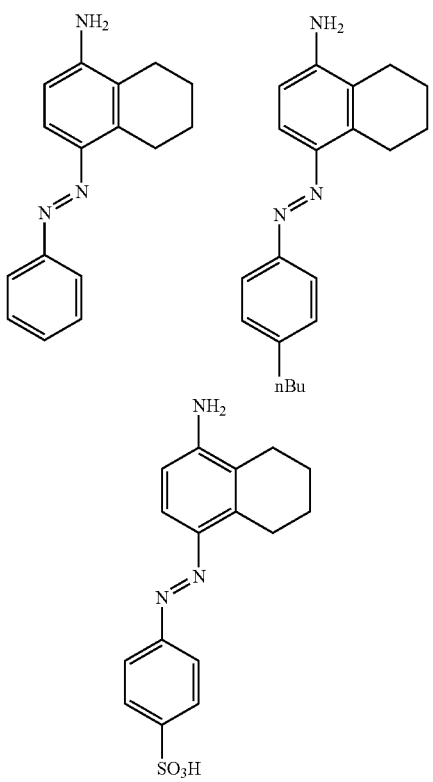

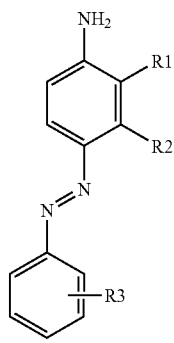

As used herein, "nBu" signifies n-butyl. In the formulae above, when the ring formed by $R_1$ and $R_2$ comprises one or two nitrogen atoms, the ring may comprise a nitrogenous divalent radical chosen from —NH— and —N($C_1$-$C_4$ alkyl) radicals, and in at least one embodiment, —NMe-.

Also disclosed herein are the intermediate compounds of formula (II):

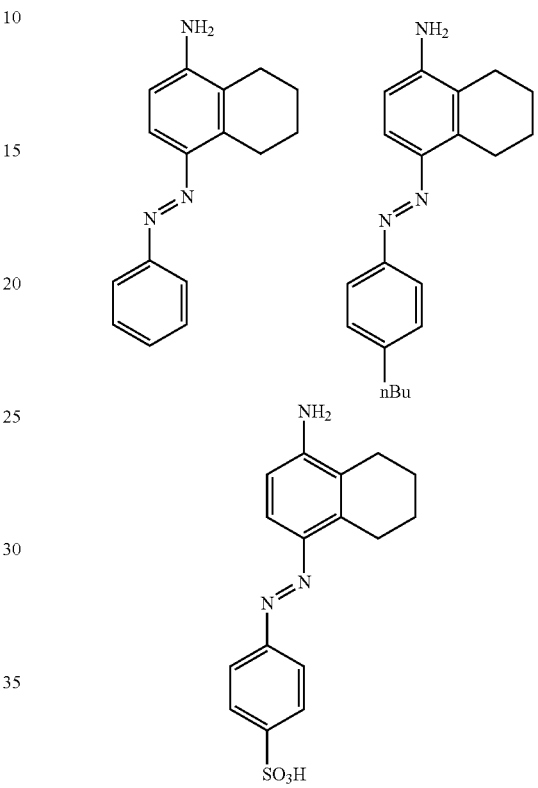

wherein $R_1$ and $R_2$ form, together with the carbon atoms to which they are attached, a 4-, 5-, 6- or 7-membered ring, wherein the ring comprises carbon atoms and, optionally, one or two atoms, which may be identical or different, chosen from oxygen and nitrogen, and when the ring comprises two atoms chosen from oxygen and nitrogen, these two atoms are non-adjacent, it being possible for the ring to be optionally substituted with at least one radical, which may be identical or different, chosen from $C_1$-$C_6$ linear or branched alkyl, hydroxyl (—OH), $C_1$-$C_6$ alkoxy, amino (—$NH_2$), $C_1$-$C_6$ (mono or dialkyl)amino, and amino($C_1$-$C_6$)alkyl radicals; and $R_3$ is chosen from hydrogen, sulphonic groups, and $C_1$-$C_4$ linear or branched alkyl radicals, with the proviso that the compound of formula (II) is not chosen from the following compounds:

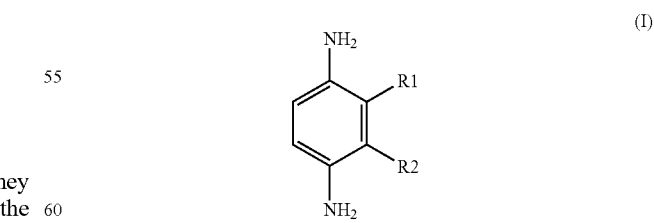

In the formulae above, when the ring formed by $R_1$ and $R_2$ comprises one or two nitrogen atoms, the ring may comprise a nitrogenous divalent radical chosen from —NH— and —N($C_1$-$C_4$ alkyl) radicals, and in at least one embodiment, —NMe-.

Further disclosed herein is a composition for the oxidation dyeing of keratin fibers, for example, human keratin fibers such as the hair, comprising, in a medium suitable for dyeing, at least one compound chosen from para-phenylenediamine compounds of formula (I) and their salts and solvates:

(I)

wherein $R_1$ and $R_2$ form, together with the carbon atoms to which they are attached, a 4-, 5-, 6-, or 7-membered ring, wherein the ring comprises carbon atoms and, optionally, one or two atoms, which may be identical or different, chosen from oxygen and nitrogen, and when the ring comprises two atoms chosen from oxygen and nitrogen, then these two atoms are non-adjacent, it being possible for the ring to be optionally substituted, for example, with at least one radical, which may be identical or different, chosen from $C_1$-$C_6$ alkyl, hydroxyl (—OH), $C_1$-$C_6$ alkoxy, (—$NH_2$) amino, $C_1$-$C_6$ (mono or dialkyl)amino, and amino($C_1$-$C_6$)alkyl radicals, with the proviso that the compound of formula (I) is not chosen from the following compounds:

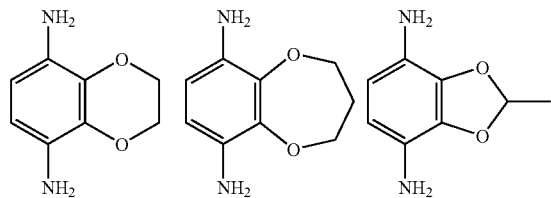

In the formulae above, when the ring formed by $R_1$ and $R_2$ comprises one or two nitrogen atoms, the ring may comprise a nitrogenous divalent radical chosen from —NH— annd —N($C_1$-$C_4$ alkyl) radicals, and in at least one embodiment, —NMe—.

The colorations obtained with the oxidation dyeing composition in accordance with the present disclosure may be strong and may exhibit excellent properties of resistance with respect to the action of the various outside agents such as light, bad weather, washing, permanent-waving, perspiration, and/or rubbing.

Still further disclosed herein is a process for the oxidation dyeing of keratin fibers comprising applying a dye composition of the present disclosure to the keratin fibers.

Other characteristics, aspects, subjects and advantages of the present disclosure will emerge more clearly upon reading the description and the examples which follow.

Examples of 2,3-disubstituted primary para-phenylenediamines of formula (I) suitable for use in the compositions for oxidation dyeing according to the present disclosure include, but are not limited to, the following compounds and their salts and/or solvates:

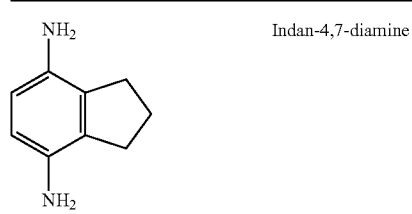

Indan-4,7-diamine

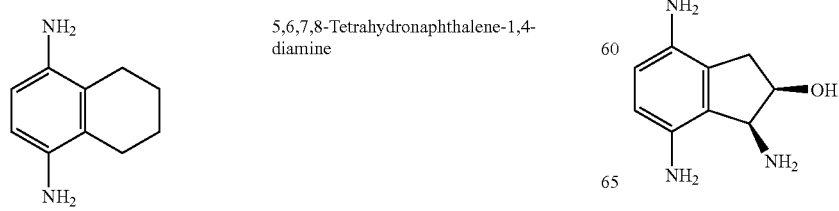

5,6,7,8-Tetrahydronaphthalene-1,4-diamine

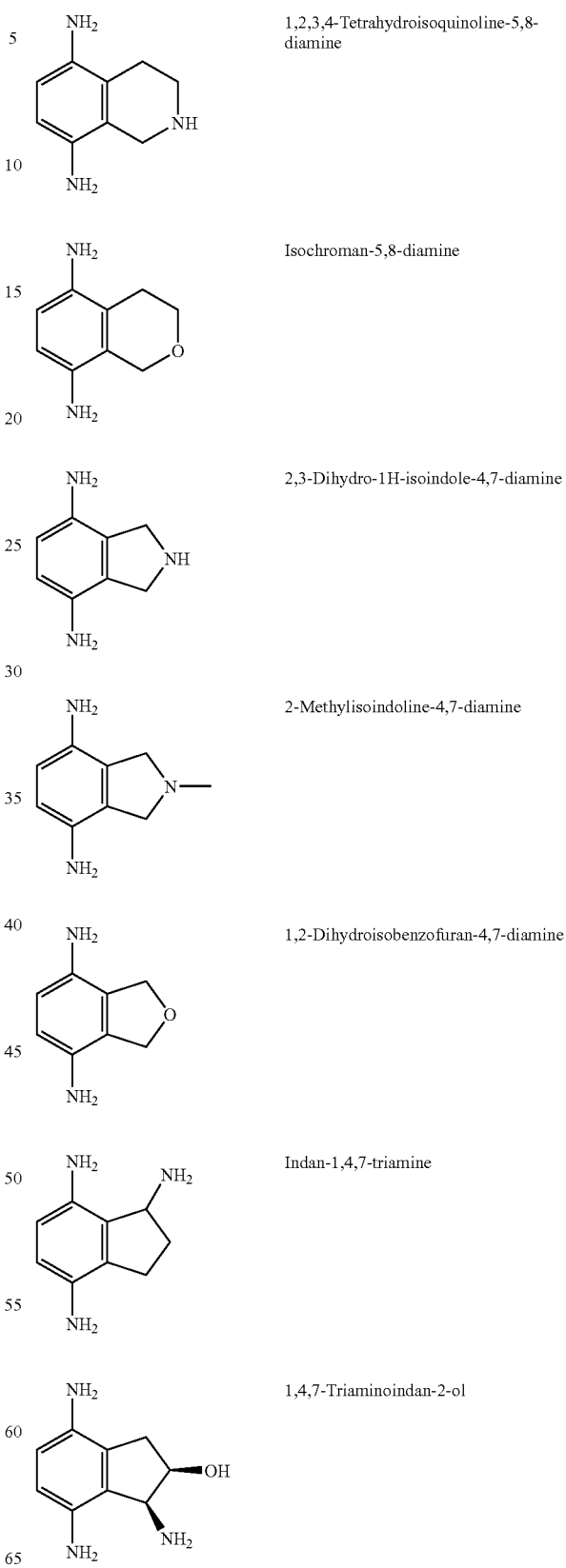

1,2,3,4-Tetrahydroisoquinoline-5,8-diamine

Isochroman-5,8-diamine 2,3-Dihydro-1H-isoindole-4,7-diamine

2-Methylisoindoline-4,7-diamine 1,2-Dihydroisobenzofuran-4,7-diamine

Indan-1,4,7-triamine 1,4,7-Triaminoindan-2-ol

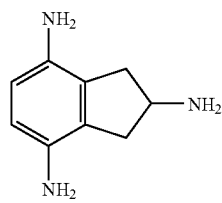 Indan-2,4,7-triamine

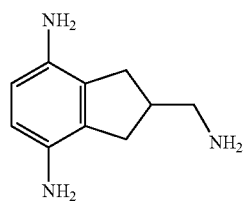 2-Aminomethylindan-4,7-diamine

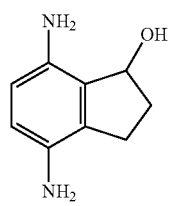 4,7-Diaminoindan-1-ol

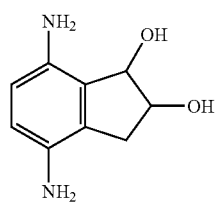 4,7-Diaminoindan-1,2-diol

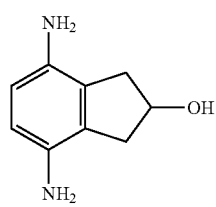 4,7-Diaminoindan-2-ol

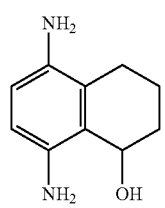 5,8-Diamino-1,2,3,4-tetrahydronaphthalen-1-ol

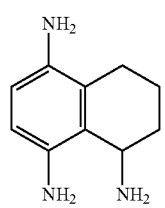 5,6,7,8-Tetrahydronaphthalene-1,4,5-triamine

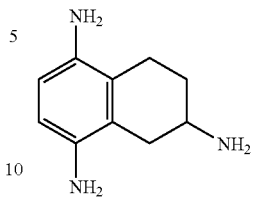 5,6,7,8-Tetrahydronaphthalene-1,4,6-triamine

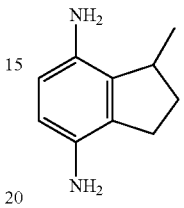 1-Methylindan-4,7-diamine

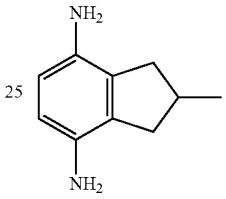 2-Methylindan-4,7-diamine

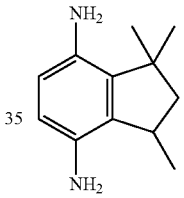 1,1,3-Trimethylindan-4,7-diamine

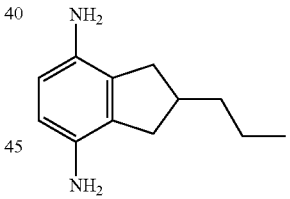 2-Propylindan-4,7-diamine

In one embodiment, the 2,3-disubstituted primary para-phenylenediamines of formula (I) useful in the compositions for oxidation dyeing may include, for example: indan-4,7-diamine, 5,6,7,8-tetrahydronaphthalene-1,4-diamine, 1,2,3,4-tetrahydroisoquinoline-5,8-diamine, 2,3-dihydro-1H-isoindole-4,7-diamine, 2-methylisoindoline-4,7-diamine, indan-2,4,7-triamine, 2-aminomethylindan-4,7-diamine, 4,7-diaminoindan-2-ol, 2-methylindan-4,7-diamine and 2-propylindan-4,7-diamine, and the physiologically acceptable salts and solvates thereof.

The 2,3-disubstituted primary para-phenylenediamines of formula (I) according to the present disclosure may be prepared, for example, according to the following general method of preparation:

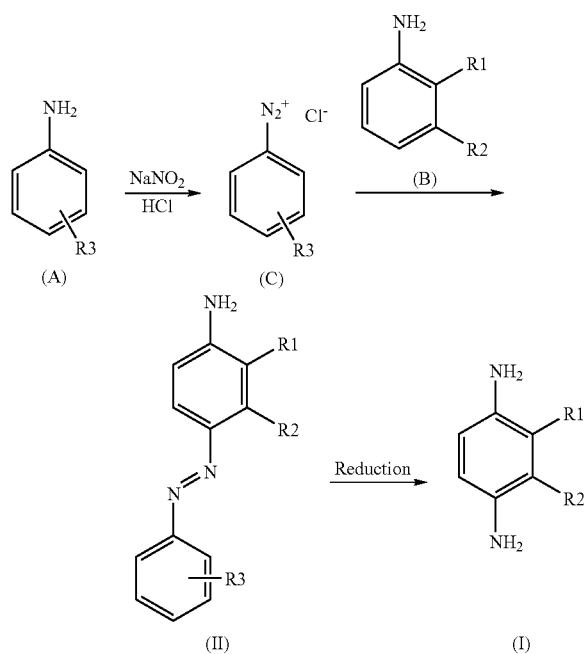

wherein $R_1$, $R_2$, and $R_3$ are defined above.

The first stage of the synthesis is the formation of an azo compound (II) by reaction of a diazonium salt (C) with an aniline (B) according to methods known in the art (see, for example, Hegarty, in Patai *The Chemistry of Diazonium and Diazo Group*, pt. 2; Wiley: New York, 1978). The second stage for obtaining the compounds (I) is a conventional reduction stage, for example, by carrying out a heterogeneous catalysis hydrogenation reaction in the presence of, for example, Pd/C, or else by carrying out a reduction reaction with sodium bisulphite, certain metals (for example, zinc) or boranes (J. March, *Advanced Organic Chemistry*, 4$^{th}$ edition, 1992, Wiley Interscience; M. Hudlicky, *Reduction in Organic Chemistry*, 1983, Ellis Honwood series Chemical Science).

A para-phenylenediamine compound of formula (I) may be obtained according to a process of synthesis which comprises reducing the corresponding intermediate compound of formula (II). As used herein, the expression "corresponding intermediate compound of formula (II)" is intended to mean that the $R_1$ radical of said "corresponding intermediate compound of formula (II)" is the same as the $R_1$ radical of the compound of formula (I) and the $R_2$ radical of said "corresponding intermediate compound of formula (II)" is the same as the $R_2$ of the compound of formula (I).

The at least one compound chosen from 2,3-disubstituted primary para-phenylenediamines of formula (I) and the salts and solvates thereof may be present in the dye composition according to the present disclosure in an amount ranging from 0.001% to 10% by weight, for example, from 0.05% to 6% by weight, or from 0.1% to 3% by weight, relative to the total weight of the dye composition.

The dye composition in accordance with the present disclosure may also comprise, in addition to the at least one 2,3-disubstituted primary para-phenylenediamine, at least one additional oxidation base which may be chosen from the oxidation bases conventionally used in oxidation dyeing, for example, additional para-phenylenediamines that are different from the 2,3-disubstituted primary para-phenylenediamines of formula (I), bisphenylalkylenediamines, para-aminophenols, ortho-aminophenols, and heterocyclic bases.

Non-limiting examples of additional para-phenylenediamines include para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline, the para-phenylenediamines described in French Patent Application No. 2 630 438, and the addition salts thereof.

Suitable bisphenylalkylenediamines may include, for example, N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and the addition salts thereof.

Examples of para-aminophenols include, but are not limited to, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and the addition salts thereof.

Non-limiting examples of ortho-aminophenols include 2-aminophenol, 2-amino-5-methylphenol, 2-amino-6-methylphenol, 5-acetamido-2-aminophenol, 5-[(2-hydroxyethyl)amino]-2-methylphenol, and the addition salts thereof.

Suitable heterocyclic bases may include, for example, pyridine derivatives, pyrimidine derivatives, pyrazole derivatives, and the addition salts thereof.

The at least one additional oxidation base may be present in the dye composition in an amount ranging from 0.0005% to 12% by weight relative to the total weight of the dye composition, for example, from 0.005% to 6% by weight.

The oxidation dyeing compositions in accordance with the present disclosure may also comprise at least one coupler and/or at least one direct dye, for example, to modify the shades and/or enrich them with tints.

The couplers suitable for use in the oxidation dyeing compositions in accordance with the present disclosure may be chosen from the couplers conventionally used in oxidation dyeing, for example, meta-phenylenediamines, meta-aminophenols, meta-diphenols, mono- or polyhydroxylated derivatives of naphthalene, and heterocyclic couplers, such as indole derivatives, pyridine derivatives, and the addition salts thereof.

According to one embodiment, these couplers may be chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

The at least one coupler may be present in the dye composition in an amount ranging from 0.0001% to 10% by weight, relative to the total weight of the dye composition, for example, from 0.005% to 5% by weight, or from 0.1% to 3% by weight.

The acid addition salts suitable for use in the dye compositions of the present disclosure (oxidation bases and couplers) may be chosen from the salts of acids chosen from hydrochloric acid, hydrobromic acid, sulphuric acid, acetic acid, lactic acid, tartaric acid, citric acid, methanesulphonic acid, and succinic acid.

The medium suitable for dyeing (or support) may be chosen from water and mixtures of water and at least one organic solvent chosen from $C_1$-$C_4$ lower alkanols, polyols and polyol ethers, aromatic alcohols, and mixtures thereof.

The dye composition according to the present disclosure may also comprise various adjuvants conventionally used in hair-dyeing compositions, such as anionic, cationic, non-ionic, amphoteric, or zwitterionic surfactants, and mixtures thereof; anionic, cationic, non-ionic, amphoteric, or zwitterionic polymers, and mixtures thereof; inorganic or organic thickeners; antioxidants; reducing agents; sunscreens; penetrating agents; sequestering agents; fragrances; buffers; dispersants; conditioning agents such as silicones; film-forming agents; preserving agents; and opacifiers.

The pH of the dye composition according to the present disclosure may range from 3 to 12.

It is understood that those skilled in the art will take care to choose the at least one additional compound in such a way that the advantageous properties intrinsically associated with the oxidation dyeing composition in accordance with the present disclosure are not, or are not substantially, impaired by the addition envisaged.

The dye composition according to the present disclosure may be in various forms, such as liquids, creams, and gels, or any other form suitable for carrying out dyeing of keratin fibers, such as the human hair.

Also disclosed herein is a process for the dyeing of keratin fibers, for example, human keratin fibers such as the hair, comprising applying at least one dye composition of the present disclosure to the keratin fibers.

According to this process, the at least one dye composition is applied to the fibers for a period of time sufficient to develop a desired coloration, either by exposure to the air, or using an oxidizing agent. The dye composition may optionally comprise oxidation catalysts in order to accelerate the oxidation process.

According to one embodiment of the present disclosure, the coloration of the fibers may be carried out without the addition of an oxidizing agent, merely by contact with the oxygen in the air.

According to another embodiment of the present disclosure, at least one dye composition as defined above is applied to the fibers, the color being revealed at acidic, neutral, or alkaline pH by means of at least one oxidizing agent, which may be added to the dye composition right at the moment of use, or which is present in an oxidizing composition separately applied simultaneously or sequentially.

According to this embodiment, the dye composition may be mixed, at the moment of use, with at least one oxidizing composition comprising, in a medium suitable for dyeing, at least one oxidizing agent present in an amount sufficient to develop a coloration. The mixture obtained may then be applied to the keratin fibers and left thereon for 3 to 50 minutes, for example, from 5 to 30 minutes, after which said fibers may be rinsed, washed with shampoo, rinsed again, and dried.

The oxidizing agent present in the oxidizing composition as defined above may be chosen from oxidizing agents conventionally used for the oxidation dyeing of keratin fibers, for example, hydrogen peroxide, urea peroxide, alkali metal bromates, and persalts, such as perborates and persulphates. In at least one embodiment, the oxidizing agent is hydrogen peroxide.

The pH of the oxidizing composition comprising the at least one oxidizing agent may be such that, after mixing with the dye composition, the pH of the resulting composition applied to the keratin fibers ranges from 3 to 12, for example, from 5 to 11. The pH may be adjusted to a desired value by means of acidifying or alkalinizing agents conventionally used in the dyeing of keratin fibers and as defined above.

The oxidizing composition may also comprise various adjuvants conventionally used in hair-dyeing compositions and as defined above.

The composition which is finally applied to the keratin fibers may be in various forms, such as liquids, creams, and gels, or any other form suitable for dyeing keratin fibers, such as the human hair.

Another subject of the present disclosure is a multicompartment dyeing device or dyeing "kit" or any other multi-compartment packing device in which a first compartment contains at least one dye composition as defined above and a second compartment contains at least one oxidizing composition as defined above. These devices may be equipped with a means for delivering the desired mixture onto the hair, such as the means described in French Patent No. 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

Synthesis Examples

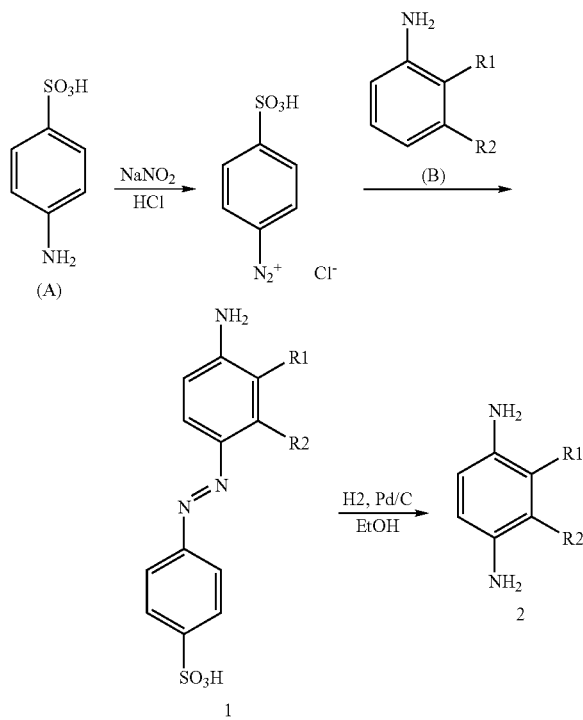

Example 1

Synthesis of Diazenylbenzenesulphonic Acid Derivatives (Compounds 1 According to the Above Scheme)

A solution of sodium nitrite in water was prepared, to which sulphanilic acid dissolved in water was added (orange color) under cold conditions. The temperature was maintained below 10° C.

The solution obtained was immediately poured into a mixture of concentrated hydrochloric acid and ice.

The cold diazonium salt was added to aniline (B) in solution in 0.5N HCl (a blood-orange color appeared), and the precipitate formed was filtered off and washed once with water.

1a) 4-[(E)-(5-Amino-1,2,3,4-tetrahydroisoquinolin-8-yl)diazenyl]benzenesulphonic acid Amine (B): 1,2,3,4-tetrahydro-5-aminosoquinoline (7.4 g, 1 eq.) in 100 ml of HCl (0.5N)
Sulphanilic acid (8.66 g, 1 eq.) in 50 ml of water
Sodium nitrite (2.8 g, 1.08 eq.) in 10 ml of water
35% Hydrochloric acid (10.8 ml, 2.5 eq.) in 60 g of ice
Mass obtained: 5.5 g (33% yield) bright red solid
M(m/z): M−=331.

1b) 4-[(E)-(7-Amino-2,3-dihydro-1H-inden-4-yl)diazenyl]benzenesulphonic acid Amine (B): 4-aminoindane (5 g, 1 eq.) in 40 ml of HCl (0.5N)
Sulphanilic acid (6.51 g, 1 eq.) in 40 ml of water
Sodium nitrite (2.8 g, 1.08 eq.) in 8 ml of water
35% Hydrochloric acid (9.5 ml, 2.5 eq.) in 50 g of ice
Mass obtained: 4.9 g (41% yield) orange solid
M(m/z): M+=318.

1c) 4-[(E)-(4-Amino-5,6,7,8-tetrahydronaphthalen-1-yl)diazenyl]benzenesulphonic acid Amine (B): 1-amino-5,6,7,8-tetrahydronaphthalene (7.36 g, 1 eq.) in 50 ml of HCl (0.5N)
Sulphanilic acid (8.66 g, 1 eq.) in 50 ml of water
Sodium nitrite (3.73 g, 1.08 eq.) in 10 ml of water
35% Hydrochloric acid (12.25 ml, 2.5 eq.) in 60 g of ice
Mass obtained: 14.58 g (88% yield) dark red solid
M(m/z): M+=332.

Example 2

Synthesis of 2,3-disubstituted para-phenylenediamines (compounds 2 according to the above scheme)

The compounds 1a, 1b, and 1c, the catalyst (palladium-on-charcoal), and the ethanol were placed, respectively, in a 0.5 liter hydrogenator.

The reduction was carried out under a hydrogen pressure approximately six bar and at a temperature of 50° C. The reaction was followed by TLC.

After filtration of the catalyst under nitrogen, the product was run into aqueous hydrochloric acid. The filtrate was evaporated to dryness under reduced pressure. The product 2 was crystallized from hydrochloric ethanol and dried at 40° C. under vacuum and over potassium hydroxide.

2a) 1,2,3,4-Tetrahydroisoquinoline-5,8-diamine dihydrochloride

Reactant 1a: (5 g)
Pd/C (1.2 g)
Absolute ethanol (250 ml)
Mass obtained: 0.33 g (9% yield) white solid
M(m/z): M+=164.

2b) Indan-4,7-diamine dihydrochloride

Reactant 1b: (4.5 g)
Pd/C (1 g)
Absolute ethanol (250 ml)
Mass obtained: 1.5 g (42% yield) pale pink solid
M(m/z): M+=149.

2c) 5,6,7,8-Tetrahydronaphthalene-1,4-diamine dihydrochloride

Reactant 1c: (5 g)
Pd/C (1 g)
Absolute ethanol (250 ml)
Mass obtained: 0.5 g (14% yield) white solid
M(m/z): M+=163.

Example 3

Synthesis of 4,7-diaminoindan-2-ol dihydrochloride (6)

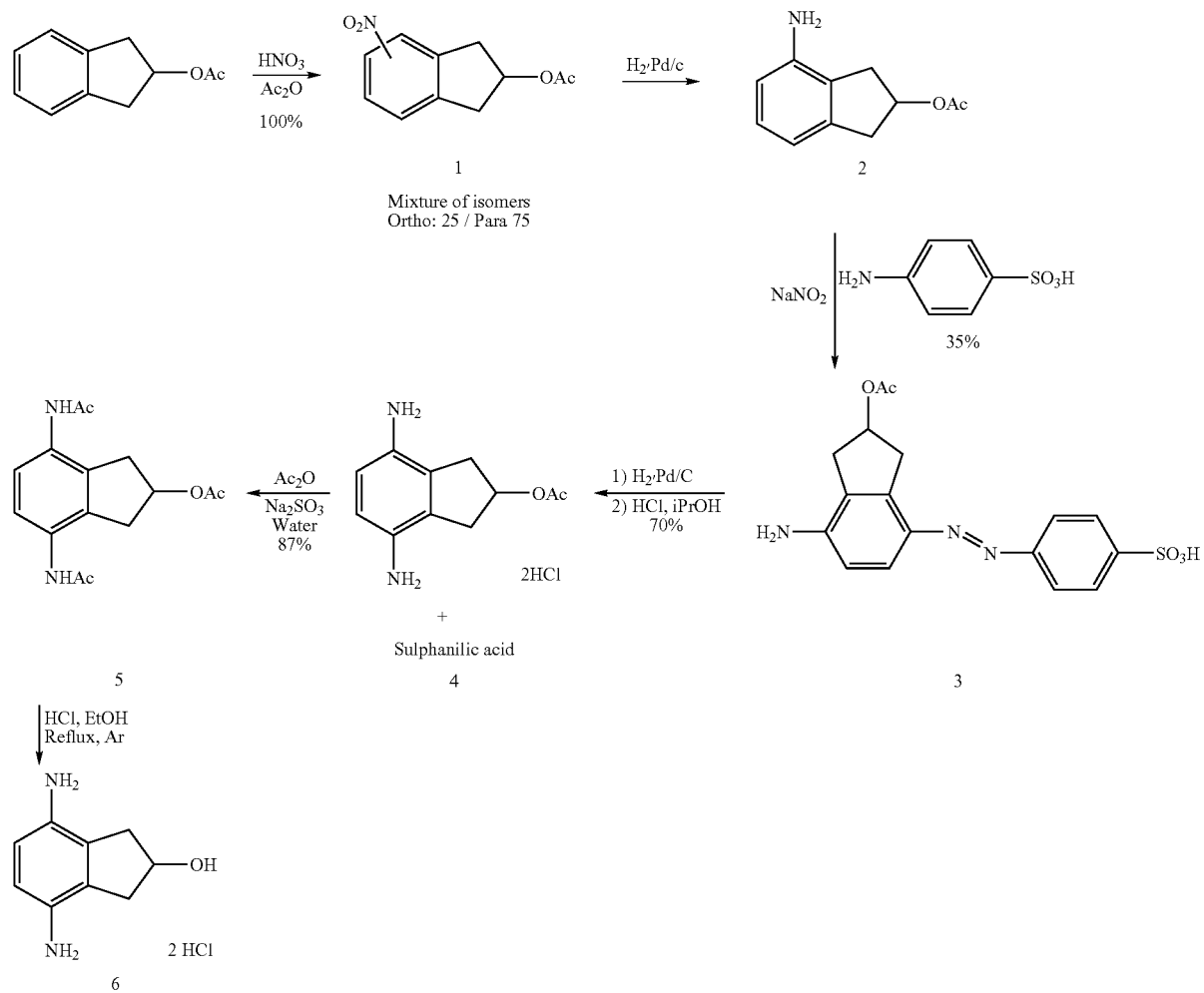

Synthesis of 4-nitro-2,3-dihydro-1H-inden-2-yl acetate (1)

33 g of 2,3-dihydro-1H-inden-2-yl acetate (1 equivalent, 0.188 mol) and 480 ml (27 equivalents, 5.08 mol) of acetic anhydride were mixed in a three-necked flask equipped with a thermometer and a dropping funnel. This mixture was cooled using an ice bath. A mixture of 120 ml (6.8 equivalents, 1.27 mol) of acetic anhydride and 39 ml of nitric acid (5 equivalents, 0.94 mol), cooled beforehand, was added dropwise to the reaction medium without exceeding 30° C. The reaction was followed by TLC. When there was no more starting product, the reaction mixture was poured into ice and extracted with ethyl acetate, washed with aqueous potassium carbonate and then with water, and, finally, the product was dried over magnesium sulphate and concentrated under vacuum.

38 g (crude yield=90%) of the mixture of ortho (67%)/para (33%) isomers (orange oil) were obtained, which mixture was recrystallized twice from ethanol in order to enrich the brown oil finally obtained in para-isomer. 18.8 g (yield=45%) of a mixture of isomers (ortho 25/para 75) of compound 1 were obtained.

Synthesis of 4-amino-2,3-dihydro-1H-inden-2-yl acetate (2)

24 g (1 equivalent, 0.108 mol) of the mixture of isomers (1) obtained above, 2.5 g of catalyst (palladium-on-charcoal) and 1.6 l of ethanol were placed in a hydrogenator.

The reduction was carried out under a hydrogen pressure of 5 bar until the starting product disappeared (followed by TLC). After filtration of the catalyst, the filtrate was evaporated to dryness under reduced pressure. 23.4 g of a brown oil were obtained, which oil was purified by preparative HPLC. 9.8 g (yield=47%) of compound 2, 99% pure by HPLC were obtained.

Synthesis of 4-{(E)-[2-(acetyloxy)-7-amino-2,3-dihydro-1H-inden-4-yl]diazenyl}benzene sulphonic acid (3)

A solution of 1.62 g of sodium nitrite (0.023 mol, 1 equivalent) in 6.8 ml of water was prepared, which solution was added, under cold conditions, to 4.07 g of sulphanilic acid (0.023 mol, 1 equivalent) dissolved in water (orange color). The temperature was maintained below 10° C.

The solution obtained was immediately poured into a mixture of concentrated hydrochloric acid (6.24 ml) and ice (31 g).

The cold diazonium salt was added to 4.5 g (0.023 mol, 1 equivalent) of aniline (2) in solution in a mixture of acetic acid (49.5 ml), water (7.5 ml), and 9.54 g of sodium acetate. A blood-orange color appeared, and the precipitate formed was filtered off and washed once with water and then with diisopropyl ether. 1.54 g of expected product (3) (yield=18%) were obtained.

Synthesis of 4,7-diamino-2,3-dihydro-1H-inden-2-yl acetate dihydrochloride as a mixture with sulphanilic acid hydrochloride (4)

2.88 g (1 equivalent, 0.0077 mol) of compound (3), 380 mg of catalyst (palladium-on-charcoal) and 600 ml of methanol were placed in a hydrogenator.

The reduction was carried out under a hydrogen pressure of 8 bar. The reaction was followed by TLC. After filtration of the catalyst under nitrogen, the product was run into hydrochloric isopropanol. The filtrate was evaporated to dryness under reduced pressure. 3.08 g of a white powder were obtained, with a yield of 82%. This powder consisted of a mixture of 4,7-diamino-2,3-dihydro-1H-inden-2-yl acetate dihydrochloride (45% by weight) and of sulphanilic acid (55% by weight).

Synthesis of 4,7-bis(acetylamino)-2,3-dihydro-1H-inden-2-yl acetate (5)

3.08 g (0.006 mol, 1 equivalent) of compound (4), 2.4 g (0.019 mol, 3 equivalents) of sodium sulphite and 30 ml of water were mixed in a three-necked flask. 1.7 ml (0.019 mol, 3 equivalents) of acetic anhydride were added dropwise to this reaction mixture, maintaining the temperature at approximately 5° C. The precipitation of a beige solid was observed. The reaction medium was stirred until it was returned to ambient temperature. The stirring was maintained for three hours. The starting product having disappeared, 7 ml of 20% aqueous ammonia were added dropwise to the reaction medium until a pH=9 was obtained. The beige solid was filtered off and then dried under vacuum. 1.59 g (yield=87%) of a beige powder were obtained.

Synthesis of 4,7-diaminoindan-2-ol dihydrochloride (6)

1.59 g of compound (5), 10 ml of ethanol and 10 ml of 37% hydrochloric acid were mixed in a three-necked flask. The reaction medium was refluxed. The reaction was followed by TLC. When the starting product and the monoacetylated product disappeared, the mixture was allowed to return to ambient temperature. The precipitate was then filtered off, washed with water and then with diisopropyl ether, and dried under vacuum. 944 mg of a white powder (yield=73%) were obtained.

The proton NMR and mass spectra were in accordance with the expected structure of the product.

Formulation Examples

Examples 1 to 13

Dye composition using indan-4,7-diamine dihydrochloride (2b)

Examples 1 to 7

Dyeing in Acidic Medium

The following dye compositions were prepared:

|  | Example | | | | | | |
|---|---|---|---|---|---|---|---|
|  | 1 | 2 | 3 | 4 | 5 | 6 | 7 |
| Indan-4,7-diamine dihydrochloride | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-diamino-phenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water q.s. | 100 g | 100 g | 100 g | 100 g | 100 g | 100 g | 100 g |

(*): Dye support (1) pH 7

| | |
|---|---|
| 96° Ethyl alcohol | 20.8 g |
| Sodium metabisulphite, 35% aqueous solution | 0.23 g A.M. |
| Pentasodium salt of diethylenetriaminepenta-acetic acid, 40% aqueous solution | 0.48 g A.M. |
| $C_8$-$C_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| $Na_2HPO_4$ | 0.28 g |
| $KH_2PO_4$ | 0.46 g |

At the moment of use, each composition was mixed with an equal weight of aqueous hydrogen peroxide at 20 volumes (6% by weight). A final pH of 7 was obtained.

Each mixture obtained was applied to locks of grey hair comprising 90% white hairs. After 30 minutes of application, the locks were rinsed, washed with a standard shampoo, rinsed again, and then dried.

The shades obtained are given in the table below:

| | Example | | | | | | |
|---|---|---|---|---|---|---|---|
| | 1 | 2 | 3 | 4 | 5 | 6 | 7 |
| Shade observed | Orangey | Deep violet-red | Deep red | Deep reddish-brown | Red | Deep blue | Deep violet |

| | |
|---|---|
| 96° Ethyl alcohol | 20.8 g |
| Sodium metabisulphite, 35% aqueous solution | 0.23 g A.M. |
| Pentasodium salt of diethylenetriaminepenta-acetic acid, 40% aqueous solution | 0.48 g A.M. |
| $C_8$-$C_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| $NH_4Cl$ | 4.32 g |
| Aqueous ammonia with 20% of $NH_3$ | 2.94 g |

At the moment of use, each composition was mixed with an equal weight of aqueous hydrogen peroxide at 20 volumes (6% by weight). A final pH of 9.5 was obtained.

Each mixture obtained was applied to locks of grey hair comprising 90% white hairs. After application for 30 minutes, the locks were rinsed, washed with a standard shampoo, rinsed again, and then dried.

The shades obtained are given in the table below:

| | Example | | | | | |
|---|---|---|---|---|---|---|
| | 8 | 9 | 10 | 11 | 12 | 13 |
| Shade observed | Deep violet-red | Deep orangey | Red | Chromatic red | Deep blue | Deep violet |

Examples 8 to 13

Dyeing in Basic Medium

The following dye compositions were prepared:

Examples 14 to 26

Dye composition using 5,6,7,8-tetrahydronaphthalene-1,4-diamine dihydrochloride (2c)

| | Example | | | | | |
|---|---|---|---|---|---|---|
| | 8 | 9 | 10 | 11 | 12 | 13 |
| Indan-4,7-diamine dihydrochloride | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |
| 1H-Indol-6-ol | | $10^{-3}$ mol | | | | |
| 2-Aminopyridin-3-ol | | | $10^{-3}$ mol | | | |
| 3,6-Dimethyl-1H-pyrazolo[5,1-c][1,2,4]triazole | | | | $10^{-3}$ mol | | |
| 2-(2,4-Diamino-phenoxy)ethanol hydrochloride | | | | | $10^{-3}$ mol | |
| 3-Amino-2-chloro-6-methylphenol hydrochloride | | | | | | $10^{-3}$ mol |
| Dye support (2) | (*) | (*) | (*) | (*) | (*) | (*) |
| Demineralized water q.s. | 100 g | 100 g | 100 g | 100 g | 100 g | 100 g |

(*): Dye support (2) pH 9.5

Examples 14 to 20

Dyeing in Acidic Medium

The following dye compositions were prepared:

|  | Example |  |  |  |  |  |  |
|---|---|---|---|---|---|---|---|
|  | 14 | 15 | 16 | 17 | 18 | 19 | 20 |
| 5,6,7,8-Tetra-hydronaphthalene-1,4-diamine dihydrochloride | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diamino-phenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water q.s. | 100 g | 100 g | 100 g | 100 g | 100 g | 100 g | 100 g |

(*): Dye support (1) pH 7

| 96° Ethyl alcohol | 20.8 g |
|---|---|
| Sodium metabisulphite, 35% aqueous solution | 0.23 g A.M. |
| Pentasodium salt of diethylenetriaminepenta-acetic acid, 40% aqueous solution | 0.48 g A.M. |
| $C_8$-$C_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| $Na_2HPO_4$ | 0.28 g |
| $KH_2PO_4$ | 0.46 g |

At the moment of use, each composition was mixed with an equal weight of aqueous hydrogen peroxide at 20 volumes (6% by weight). A final pH of 7 was obtained.

Each mixture obtained was applied to locks of grey hair comprising 90% white hairs. After application for 30 minutes, the locks were rinsed, washed with a standard shampoo, rinsed again, and then dried.

The shades obtained are given in the table below:

|  | Example |  |  |  |  |  |  |
|---|---|---|---|---|---|---|---|
|  | 14 | 15 | 16 | 17 | 18 | 19 | 20 |
| Shade observed | Orangey | Deep violet-red | Deep red | Deep reddish-brown | Red | Deep blue | Deep violet-blue |

Examples 21 to 26

Dyeing in Basic Medium

The following dye compositions were prepared:

|  | Example |  |  |  |  |  |
|---|---|---|---|---|---|---|
|  | 21 | 22 | 23 | 24 | 25 | 26 |
| 5,6,7,8-Tetra-hydronaphthalene-1,4-diamine dihydrochloride | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |
| 1H-Indol-6-ol | | $10^{-3}$ mol | | | | |
| 2-Aminopyridin-3-ol | | | $10^{-3}$ mol | | | |
| 3,6-Dimethyl-1H-pyrazolo[5,1-c][1,2,4]triazole | | | | $10^{-3}$ mol | | |
| 2-(2,4-Diamino-phenoxy)ethanol hydrochloride | | | | | $10^{-3}$ mol | |

-continued

|  | Example | | | | | |
|---|---|---|---|---|---|---|
|  | 21 | 22 | 23 | 24 | 25 | 26 |
| 3-Amino-2-chloro-6-methylphenol hydrochloride |  |  |  |  |  | $10^{-3}$ mol |
| Dye support (2) | (*) | (*) | (*) | (*) | (*) | (*) |
| Demineralized water q.s. | 100 g | 100 g | 100 g | 100 g | 100 g | 100 g |

(*): Dye support (2) pH 9.5

| | |
|---|---|
| 96° Ethyl alcohol | 20.8 g |
| Sodium metabisulphite, 35% aqueous solution | 0.23 g A.M. |
| Pentasodium salt of diethylenetriaminepenta-acetic acid, 40% aqueous solution | 0.48 g A.M. |
| $C_8$-$C_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| $NH_4Cl$ | 4.32 g |
| Aqueous ammonia with 20% of $NH_3$ | 2.94 g |

At the moment of use, each composition was mixed with an equal weight of aqueous hydrogen peroxide at 20 volumes (6% by weight). A final pH of 9.5 was obtained.

Each mixture obtained was applied to locks of grey hair comprising 90% white hairs. After application for 30 minutes, the locks were rinsed, washed with a standard shampoo, rinsed again, and then dried.

The shades obtained are given in the table below:

| | Example | | | | | |
|---|---|---|---|---|---|---|
| | 21 | 22 | 23 | 24 | 25 | 26 |
| Shade observed | Deep violet | Orangey | Orangey | Chromatic red | Deep blue | Deep violet-blue |

Examples 27 to 33

Dye composition using 1,2,3,4-tetrahydroisoquinoline-5,8-diamine dihydrochloride Examples 27 to 30

Dyeing in Acidic Medium

The following dye compositions were prepared:

|  | Example | | | |
|---|---|---|---|---|
|  | 27 | 28 | 29 | 30 |
| 1,2,3,4-Tetrahydroisoquinoline-5,8-diamine dihydrochloride | $10^{-3}$ mol | $10^{-3}$ mol | $10^{-3}$ mol | $10^{-3}$ mol |
| 5-Amino-2-methylphenol | $10^{-3}$ mol |  |  |  |
| 1H-Indol-6-ol |  | $10^{-3}$ mol |  |  |
| 2-(2,4-Diaminophenoxy)ethanol hydrochloride |  |  | $10^{-3}$ mol |  |
| 3-Amino-2-chloro-6-methylphenol hydrochloride |  |  |  | $10^{-3}$ mol |
| Dye support (2) | (*) | (*) | (*) | (*) |
| Demineralized water q.s. | 100 g | 100 g | 100 g | 100 g |

(*): Dye support (1) pH 7

| | |
|---|---|
| 96° Ethyl alcohol | 20.8 g |
| Sodium metabisulphite, 35% aqueous solution | 0.23 g A.M. |
| Pentasodium salt of diethylenetriaminepenta-acetic acid, 40% aqueous solution | 0.48 g A.M. |
| $C_8$-$C_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| $Na_2HPO_4$ | 0.28 g |
| $KH_2PO_4$ | 0.46 g |

At the moment of use, each composition was mixed with an equal weight of aqueous hydrogen peroxide at 20 volumes (6% by weight). A final pH of 7 was obtained.

Each mixture obtained was applied to locks of grey hair comprising 90% white hairs. After application for 30 minutes, the locks were rinsed, washed with a standard shampoo, rinsed again, and then dried.

The shades obtained are given in the table below:

|  | Example | | | |
| --- | --- | --- | --- | --- |
|  | 27 | 28 | 29 | 30 |
| Shade observed | Red | Orangey | Grey-blue | Violet-red |

Examples 31 to 33

Dyeing in Basic Medium

The following dye compositions were prepared:

|  | Example | | |
| --- | --- | --- | --- |
|  | 31 | 32 | 33 |
| 1,2,3,4-Tetrahydroisoquinoline-5,8-diamine dihydrochloride | $10^{-3}$ mol | $10^{-3}$ mol | $10^{-3}$ mol |
| 5-Amino-2-methylphenol | $10^{-3}$ mol |  |  |
| 2-(2,4-Diaminophenoxy)ethanol hydrochloride |  | $10^{-3}$ mol |  |
| 3-Amino-2-chloro-6-methylphenol hydrochloride |  |  | $10^{-3}$ mol |
| Dye support (1) | (*) | (*) | (*) |
| Demineralized water q.s. | 100 g | 100 g | 100 g |

(*): Dye support (2) pH 9.5

At the moment of use, each composition was mixed with an equal weight of aqueous hydrogen peroxide at 20 volumes (6% by weight). A final pH of 9.5 was obtained.

Each mixture obtained was applied to locks of grey hair comprising 90% white hairs. After application for 30 minutes, the locks were rinsed, washed with a standard shampoo, rinsed again, and then dried.

The shades obtained are given in the table below:

|  | Example | | |
| --- | --- | --- | --- |
|  | 31 | 32 | 33 |
| Shade observed | Red | Blue | Violet-red |

Examples 34 to 41

Dye composition using 4,7-diaminoindan-2-ol dihydrochloride

Examples 34 to 38

Dyeing in Acidic Medium

The following dye compositions were prepared:

|  | Example | | | | |
| --- | --- | --- | --- | --- | --- |
|  | 34 | 35 | 36 | 37 | 38 |
| 4,7-Diaminoindan-2-ol dihydrochloride | $10^{-3}$ mol | $10^{-3}$ mol | $10^{-3}$ mol | $10^{-3}$ mol | $10^{-3}$ mol |
| 5-Amino-2-methylphenol | $10^{-3}$ mol |  |  |  |  |
| 1H-Indol-6-ol |  | $10^{-3}$ mol |  |  |  |
| 2-Aminopyridin-3-ol |  |  | $10^{-3}$ mol |  |  |
| 2-(2,4-Diaminophenoxy)ethanol hydrochloride |  |  |  | $10^{-3}$ mol |  |
| 3-Amino-2-chloro-6-methylphenol hydrochloride |  |  |  |  | $10^{-3}$ mol |
| Dye support (2) | (*) | (*) | (*) | (*) | (*) |
| Demineralized water q.s. | 100 g | 100 g | 100 g | 100 g | 100 g |

(*): Dye support (1) pH 7

| 96° Ethyl alcohol | 20.8 g |
| --- | --- |
| Sodium metabisulphite, 35% aqueous solution | 0.23 g A.M. |
| Pentasodium salt of diethylenetriaminepenta-acetic acid, 40% aqueous solution | 0.48 g A.M. |
| C$_8$-C$_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| NH$_4$Cl | 4.32 g |
| Aqueous ammonia with 20% of NH$_3$ | 2.94 g |

| 96° Ethyl alcohol | 20.8 g |
| --- | --- |
| Sodium metabisulphite, 35% aqueous solution | 0.23 g A.M. |
| Pentasodium salt of diethylenetriaminepenta-acetic acid, 40% aqueous solution | 0.48 g A.M. |
| C$_8$-C$_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| Na$_2$HPO$_4$ | 0.28 g |
| KH$_2$PO$_4$ | 0.46 g |

At the moment of use, each composition was mixed with an equal weight of aqueous hydrogen peroxide at 20 volumes (6% by weight). A final pH of 7 was obtained.

Each mixture obtained was applied to locks of grey hair comprising 90% white hairs. After application for 30 minutes, the locks were rinsed, washed with a standard shampoo, rinsed again, and then dried.

The shades obtained are given in the table below:

|  | Example | | | | |
| --- | --- | --- | --- | --- | --- |
|  | 34 | 35 | 36 | 37 | 38 |
| Shade observed | Red | Orangey | Reddy-brown | Deep grey-blue | Violet |

Examples 39 to 41

Dyeing in Basic Medium

The following dye compositions were prepared:

|  | Example | | |
| --- | --- | --- | --- |
|  | 39 | 40 | 41 |
| 4,7-Diaminoindan-2-ol dihydrochloride | $10^{-3}$ mol | $10^{-3}$ mol | $10^{-3}$ mol |
| 5-Amino-2-methylphenol | $10^{-3}$ mol | | |
| 2-(2,4-Diaminophenoxy)ethanolhydrochloride | | $10^{-3}$ mol | |
| 3-Amino-2-chloro-6-methylphenolhydrochloride | | | $10^{-3}$ mol |
| Dye support (2) | (*) | (*) | (*) |
| Demineralized water q.s. | 100 g | 100 g | 100 g |

(*): Dye support (2) pH 9.5

| 96° Ethyl alcohol | 20.8 g |
| --- | --- |
| Sodium metabisulphite, 35% aqueous solution | 0.23 g A.M. |
| Pentasodium salt of diethylenetriaminepenta-acetic acid, 40% aqueous solution | 0.48 g A.M. |
| $C_8$-$C_{10}$ Alkyl polyglucoside, 60% aqueous solution | 3.6 g A.M. |
| Benzyl alcohol | 2.0 g |
| Polyethylene glycol with 8 ethylene oxide units | 3.0 g |
| $NH_4Cl$ | 4.32 g |
| Aqueous ammonia with 20% of $NH_3$ | 2.94 g |

At the moment of use, each composition was mixed with an equal weight of aqueous hydrogen peroxide at 20 volumes (6% by weight). A final pH of 9.5 was obtained.

Each mixture obtained was applied to locks of grey hair comprising 90% white hairs. After application for 30 minutes, the locks were rinsed, washed with a standard shampoo, rinsed again, and then dried.

The shades obtained are given in the table below:

|  | Example | | |
| --- | --- | --- | --- |
|  | 39 | 40 | 41 |
| Shade observed | Red | Grey-blue | Violet |

What is claimed is:

1. A para-phenylenediamine compound chosen from compounds of formula (I), and physiologically acceptable solvates and acid salts thereof:

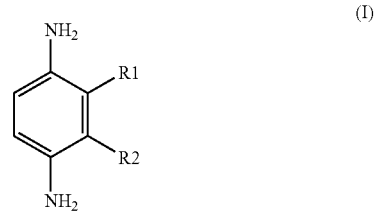

wherein $R_1$ and $R_2$ form, together with the carbon atoms to which they are attached, a 4-, 5-, 6-, or 7-membered ring, wherein the ring comprises carbon atoms and, optionally, one or two atoms chosen from oxygen and nitrogen, it being possible for the ring to be substituted, with the proviso that when the ring comprises two atoms chosen from oxygen and nitrogen, these two atoms are non-adjacent, and with the further proviso that the para-phenylenediamine compound is not chosen from the following compounds:

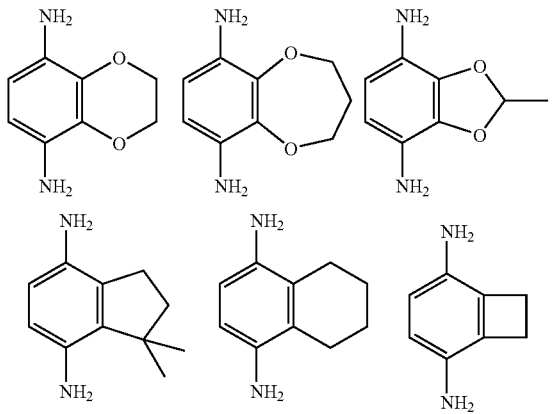

2. The compound of claim 1, wherein $R_1$ and $R_2$ form, together with the carbon atoms to which they are attached, a 5- or 6-membered ring.

3. The compound of claim 1, wherein the ring comprises carbon atoms and, optionally, one atom chosen from oxygen and nitrogen.

4. The compound of claim 1, wherein the ring is optionally substituted with at least one radical, which may be identical or different, chosen from $C_1$-$C_6$ linear or branched alkyl, hydroxyl (—OH), $C_1$-$C_6$ alkoxy, amino (—NH$_2$), $C_1$-$C_6$ (mono or dialkyl)amino, and amino($C_1$-$C_6$)alkyl radicals.

5. The compound of claim 4, wherein the ring is substituted with 1, 2, or 3 radicals chosen from $C_1$-$C_3$ alkyl, hydroxyl (—OH), amino (—NH$_2$), and amino($C_1$-$C_3$)alkyl radicals.

6. The compound of claim 1, wherein the ring is a carbon-based ring with 5 or 6 ring members.

7. The compound of claim 1, wherein the ring is a 5- or 6-membered ring comprising a divalent radical chosen from —NH— and —NMe- radicals.

8. The compound of claim 1, chosen from the following compounds and their physiologically acceptable salts and solvates:

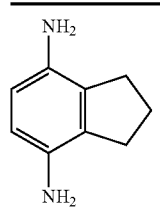
Indan-4,7-diamine

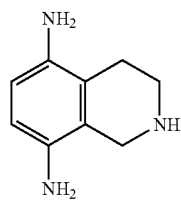
1,2,3,4-Tetrahydroisoquinoline-5,8-diamine

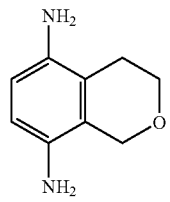
Isochroman-5,8-diamine

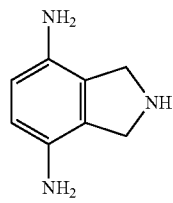
2,3-Dihydro-1H-isoindole-4,7-diamine

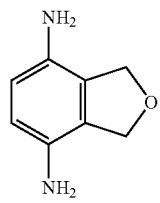
1,3-Dihydroisobenzofuran-4,7-diamine

-continued

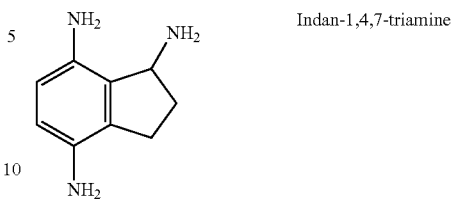
Indan-1,4,7-triamine

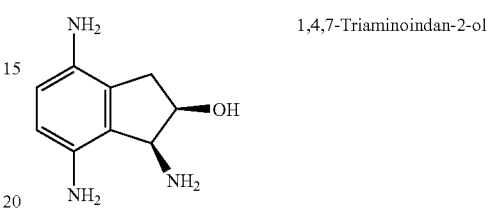
1,4,7-Triaminoindan-2-ol

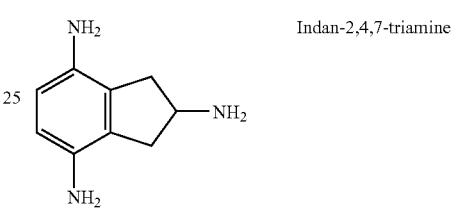
Indan-2,4,7-triamine

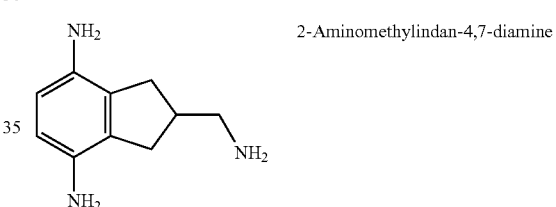
2-Aminomethylindan-4,7-diamine

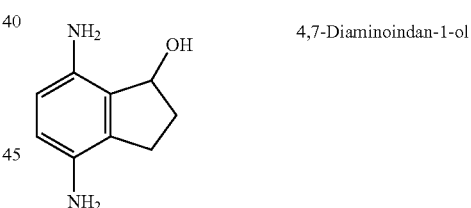
4,7-Diaminoindan-1-ol

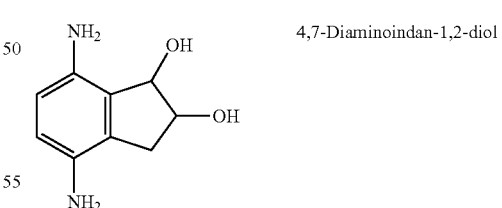
4,7-Diaminoindan-1,2-diol

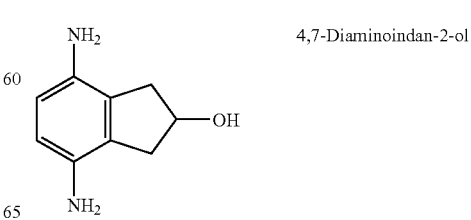
4,7-Diaminoindan-2-ol

-continued

| | |
|---|---|
| 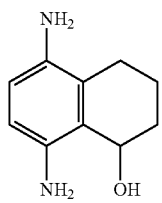 | 5,8-Diamino-1,2,3,4-tetrahydronaphthalen-1-ol |
| 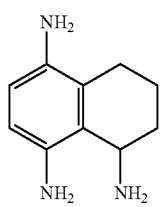 | 5,6,7,8-Tetrahydronaphthalene-1,4,5-triamine |
| 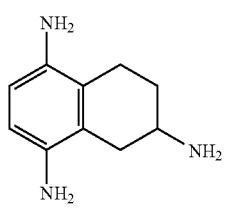 | 5,6,7,8-Tetrahydronaphthalene-1,4,6-triamine |
| 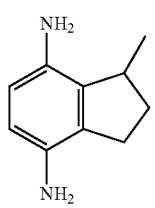 | 1-Methylindan-4,7-diamine |
| 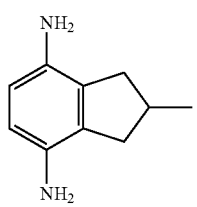 | 2-Methylindan-4,7-diamine |
| 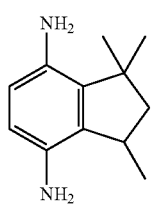 | 1,1,3-Trimethylindan-4,7-diamine |
| 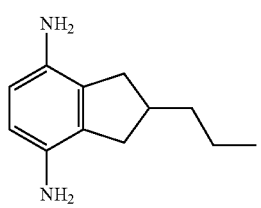 | 2-Propylindan-4,7-diamine |

-continued

| | |
|---|---|
| 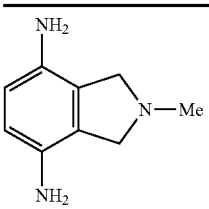 | 2-Methylisoindoline-4,7-diamine. |

9. The compound of claim 1, chosen from indan-4,7-diamine, 1,2,3,4-tetrahydroisoquinoline-5,8-diamine, 2,3-dihydro-1H-isoindole-4,7-diamine, 2-methylisoindoline-4,7-diamine, indan-2,4,7-triamine, 2-aminomethylindan-4,7-diamine, 4,7-diaminoindan-2-ol, 2-methylindan-4,7-diamine and 2-propylindan-4,7-diamine, and their physiologically acceptable salts and solvates.

10. A process for the synthesis of a para-phenylenediamine compound of formula (I):

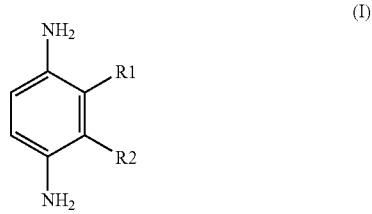

wherein:

$R_1$ and $R_2$ form, together with the carbon atoms to which they are attached, a 4-, 5-, 6-, or 7-membered ring, wherein the ring comprises carbon atoms and, optionally, one or two atoms chosen from oxygen and nitrogen, it being possible for the ring to be substituted, with the proviso that when the ring comprises two atoms chosen from oxygen and nitrogen, these two atoms are non-adjacent, and with the further proviso that the para-phenylenediamine compound is not chosen from the following compounds:

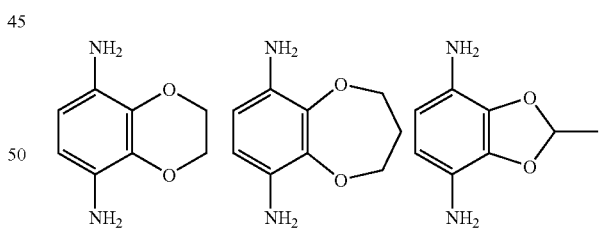

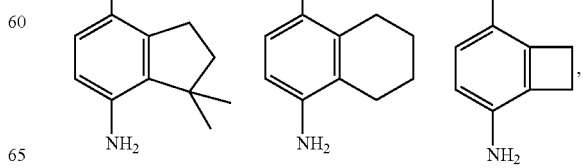

the process comprising reducing the corresponding intermediate compound of formula (II):

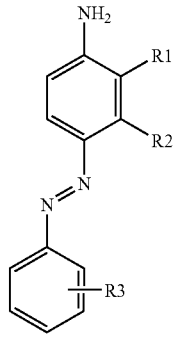

wherein:
$R_1$ and $R_2$ form, together with the carbon atoms to which they are attached, a 4-, 5-, 6-, or 7-membered ring, wherein the ring comprises carbon atoms and, optionally, one or two atoms chosen from oxygen and nitrogen, it being possible for the ring to be substituted; with the proviso that when the ring comprises two atoms chosen from oxygen and nitrogen, these two atoms are non-adjacent; and $R_3$ is chosen from hydrogen, sulphonic groups, and $C_1$-$C_4$ linear or branched alkyl radicals, with the proviso that the compounds of formula (II) are not chosen from the following:

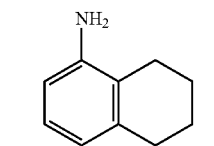 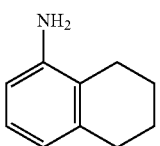

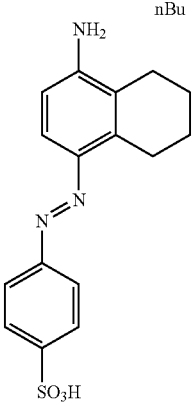

11. An intermediate compound of formula (II):

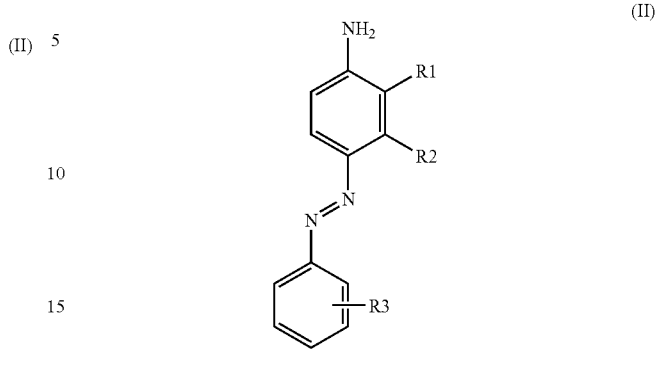

wherein
$R_1$ and $R_2$ form, together with the carbon atoms to which they are attached, a 4-, 5-, 6- or 7-membered ring, wherein the ring comprises carbon atoms and, optionally, one or two atoms chosen from oxygen and nitrogen, it being possible for the ring to be optionally substituted; with the proviso that when the ring comprises two atoms chosen from oxygen and nitrogen, these two atoms are non-adjacent; and $R_3$ is chosen from hydrogen, sulphonic groups, and $C_1$-$C_4$ linear or branched alkyl radicals, with the proviso that the compounds of formula (II) are not chosen from the following:

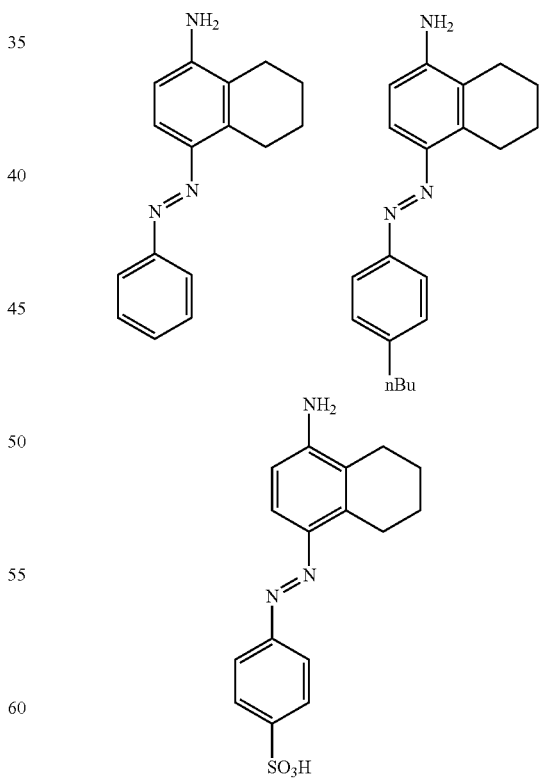

12. A composition for the oxidation dyeing of keratin fibers, comprising, in a medium suitable for dyeing, at least one para-phenylenediamine compound chosen from para-phenylenediamine compounds of formula (I) and their physiologically acceptable solvates and acid salts:

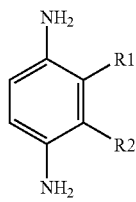

wherein $R_1$ and $R_2$ form, together with the carbon atoms to which they are attached, a 4-, 5-, 6-, or 7-membered ring, wherein the ring comprises carbon atoms and, optionally, one or two atoms chosen from oxygen and nitrogen, it being possible for the ring to be optionally substituted, with the proviso that when the ring comprises two atoms chosen from oxygen and nitrogen, these two atoms are non-adjacent, and with the further proviso that the at least one para-phenylenediamine compound is not chosen from:

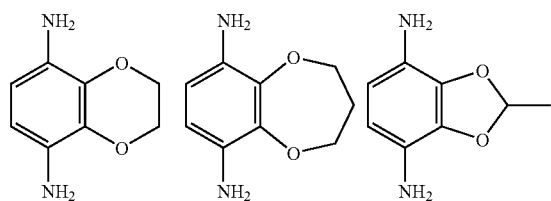

13. The composition of claim 12, wherein the ring formed by $R_1$ and $R_2$ with the carbon atoms to which they are attached is a carbon-based or nitrogenous ring.

14. The composition of claim 12, wherein the at least one para-phenylenediamine compound is chosen from: indan-4,7-diamine, 5,6,7,8-tetrahydronaphthalene-1,4-diamine, 1,2,3,4-tetrahydroisoquinoline-5,8-diamine, isochroman-5,8-diamine, 2,3-dihydro-1H-isoindole-4,7-diamine, 2-methylisoindoline-4,7-diamine, 1,3-dihydroisobenzofuran-4,7-diamine, indan-1,4,7-triamine, 1,4,7-triaminoindan-2-ol, indan-2,4,7-triamine, 2-aminomethylindan-4,7-diamine, 4,7-diaminoindan-1-ol, 4,7-diaminoindan-1,2-diol, 4,7-diaminoindan-2-ol, 5,8-diamino-1,2,3,4-tetrahydronaphthalen-1-ol, 5,6,7,8-tetrahydronaphthalene-1,4,5-triamine, 5,6,7,8-tetrahydronaphthalene-1,4,6-triamine, 1-methylindan-4,7-diamine, 2-methylindan-4,7-diamine, 1,1,3-trimethylindan-4,7-diamine and 2-propylindan-4,7-diamine, and their physiologically acceptable salts and solvates.

15. The composition of claim 14, wherein the at least one para-phenylenediamine compound is chosen from indan-4,7-diamine, 5,6,7,8-tetrahydronaphthalene-1,4-diamine, 1,2,3,4-tetrahydroisoquinoline-5,8-diamine, 2,3-dihydro-1H-isoindole-4,7-diamine, 2-methylisoindoline-4,7-diamine, indan-2,4,7-triamine, 2-aminomethylindan-4,7-diamine, 4,7-diaminoindan-2-ol, 2-methylindan-4,7-diamine and 2-propylindan-4,7-diamine, and the physiologically acceptable salts and solvates thereof.

16. The composition of claim 12, wherein the at least one para-phenylenediamine compound is present in an amount ranging from 0.001% to 10% by weight, relative to the total weight of the composition.

17. The composition of claim 16, wherein the at least one para-phenylenediamine compound is present in an amount ranging from 0.1% to 3% by weight, relative to the total weight of the composition.

18. The composition of claim 17, wherein the at least one para-phenylenediamine compound is present in an amount ranging from 0.05% to 6% by weight, relative to the total weight of the composition.

19. The composition of claim 12, wherein the medium suitable for dyeing is chosen from water and mixtures of water and at least one organic solvent chosen from $C_1$-$C_4$ lower alkanols, polyols and polyol ethers, aromatic alcohols, and mixtures thereof.

20. The composition of claim 12, wherein the composition has a pH ranging from 3 to 12.

21. The composition of claim 12, further comprising at least one additional oxidation base chosen from para-phenylenediamines that are different from the para-phenylenediamines of formula (I), bisphenylalkylenediamines, para-aminophenols, ortho-aminophenols, heterocyclic bases, and the addition salts thereof.

22. The composition of claim 21, wherein the at least one additional oxidation base is present in the composition in an amount ranging from 0.0005% to 12% by weight, relative to the total weight of the composition.

23. The composition of claim 12, further comprising at least one coupler and/or at least one direct dye.

24. The composition of claim 23, wherein the at least one coupler is chosen from meta-phenylenediamines, meta-aminophenols, meta-diphenols, mono- or polyhydroxylated derivatives of naphthalene, heterocyclic couplers, and their acid addition salts.

25. The composition of claim 23, wherein the at least one coupler is present in the composition in an amount ranging from 0.0001% to 10% by weight, relative to the total weight of the composition.

26. The composition of claim 12, wherein the acid addition salts are chosen from salts of hydrochloric acid, hydrobromic acid, sulphuric acid, acetic acid, lactic acid, tartaric acid, citric acid, methanesulphonic acid, para-toluenesulphonic acid, benzenesulphonic acid, phosphoric acid, and succinic acid.

27. A process for the oxidation dyeing of keratin fibers, comprising applying at least one dye composition to the keratin fibers for a period of time sufficient to develop a desired coloration, either by exposure to the air, or using at least one oxidizing agent, optionally in the presence of at least one oxidation catalyst; wherein the at least one dye composition comprises, in a medium suitable for dyeing, at least one para-phenylenediamine compound chosen from para-phenylenediamine compounds of formula (I) and their physiologically acceptable solvates and acid salts:

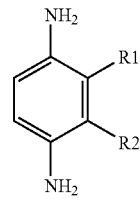

wherein $R_1$ and $R_2$ form, together with the carbon atoms to which they are attached, a 4-, 5-, 6-, or 7-membered ring, wherein the ring comprises carbon atoms and, optionally, one or two atoms chosen from oxygen and nitrogen, it being possible for the ring to be optionally substituted, with the proviso that when the ring comprises two atoms chosen from oxygen and nitrogen, these two atoms are non-adjacent, and with the further proviso that the at least one para-phenylenediamine compound is not chosen from the following:

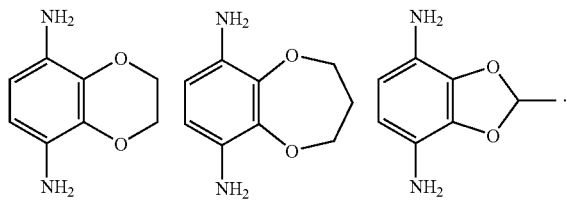

28. The process of claim 27, wherein the keratin fibers are human keratin fibers.

29. The process of claim 28, wherein the human keratin fibers are hair.

30. The process of claim 27, wherein the coloration is revealed by contact with the oxygen in the air.

31. The process of claim 27, wherein the color is revealed at acidic, neutral, or alkaline pH by means of at least one oxidizing agent, which is added to the dye composition at the moment of use, or which is present in an oxidizing composition separately applied simultaneously or sequentially.

32. The process of claim 27, wherein the at least one oxidizing agent is chosen from hydrogen peroxide, urea peroxide, alkali metal bromates, and persalts.

33. The process of claim 32, wherein the persalts are chosen from perborates and persulphates.

34. A multicompartment dyeing kit, comprising at least one first compartment containing at least one dye composition, and at least one second compartment containing at least one oxidizing composition; wherein the at least one dye composition comprises, in a medium suitable for dyeing, at least one para-phenylenediamine compound chosen from para-phenylenediamine compounds of formula (I) and their physiologically acceptable solvates and acid salts:

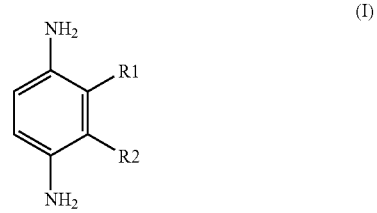

(I)

wherein $R_1$ and $R_2$ form, together with the carbon atoms to which they are attached, a 4-, 5-, 6-, or 7-membered ring, wherein the ring comprises carbon atoms and, optionally, one or two atoms chosen from oxygen and nitrogen, it being possible for the ring to be optionally substituted, with the proviso that when the ring comprises two atoms chosen from oxygen and nitrogen, these two atoms are non-adjacent, and with the further proviso that the at least one para-phenylenediamine compound is not chosen from the following:

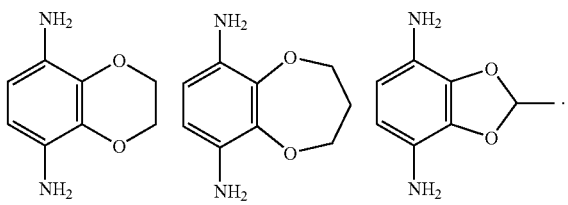

* * * * *